US00PP16183P2

(12) United States Plant Patent
Korlipara

(10) Patent No.: US PP16,183 P2
(45) Date of Patent: Jan. 3, 2006

(54) ***ECHINACEA PURPUREA* PLANT NAMED 'LITTLE GIANT'**

(50) Latin Name: *Echinacea purpurea*
Varietal Denomination: Little Giant

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 116 days.

(21) Appl. No.: 10/872,349

(22) Filed: Jun. 18, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Echinacea purpurea* plant named 'Little Giant' characterized by its unique flowers with numerous red purple rays that radiate out, orange cone, lovely fragrance, and an upright dwarf habit.

1 Drawing Sheet

Botanical classification: *Echinacea purpurea.*
Variety designation: 'Little Giant'.

The present invention relates to a new and distinct cultivar of *Echinacea purpurea* and given the cultivar name 'Little Giant'. *Echinacea* is in the family Asteraceae. This new cultivar originated as a whole plant mutation in a mass planting of *Echinacea purpurea* 'Ruby Giant' (an unpatented plant) in the nursery trial fields in Canby, Oreg.

This new *Echinacea purpurea* cultivar is distinguished by:

1. Large red purple flowers with a double row of ray flowers.
2. Dwarf habit.
3. Lovely fragrance.
4. Ray flowers which spread out parallel to ground, slightly ruffled.
5. Strong upright stems.
6. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with changes in the environment without a change in the genotype of the plant.

BRIEF DESCRIPTION OF THE DRAWING

The photograph shows *Echinacea purpurea* 'Little Giant' growing in the ground in field trials in the summer in Canby, Oreg.

DETAILED PLANT DESCRIPTION

The following is a detailed description of the new *Echinacea purpurea* cultivar based on observations of a one-year-old specimen growing in the trial fields in Canby, Oreg. The color descriptions are all based on The Royal Horticultural Society Colour Chart.

Botanical classification: *Echinacea purpurea.*
Variety denomination: 'Little Giant'.

Plant:
- *Type.*—Herbaceous perennial.
- *Hardiness.*—USDA Zones 4 to 9.
- *Size.*—30 cm wide and 40 cm. tall to top of flowers.
- *Form.*—Basal clump.

Leaf:
- *Type.*—Simple.
- *Shape.*—Lanceolate.
- *Arrangement.*—Alternate.
- *Blade length.*—10 to 19 cm.
- *Width.*—3 to 6 cm. at the widest part.
- *Margins.*—Slightly undulate and broadly crenate.
- *Apex.*—Acuminate.
- *Base.*—Attenuate, continuing down petiole.
- *Texture.*—Rough.
- *Vestiture.*—Strigose.
- *Venation.*—Pinnate.
- *Color.*—Topside — Deep Green, Between Green 139A and Yellow Green 147A. Bottom — Yellow Green 147B.
- *Petiole length.*—8 to 11 cm if basal leaf, 0.5 to 1 cm if cauline leaf.
- *Petiole vestiture.*—Strigose.
- *Petiole color.*—Greyed Purple 187B except Yellow Green 146D on back.

Inflorescence:
- *Type.*—Long stalked terminal heads.
- *Number of heads per plant.*—12 in first flush.
- *Immature inflorescence.*—While still developing the ray petals are slightly upright and Red Purple 64A. The closed disc is Greyed Purple 187A, occasionally the very center may be Yellow Green 144A. Disc size ranges from 4 cm to 4.8 cm wide.
- *Peduncle.*—Strong and fibrous, makes a good cut flower. Height: 40 cm. Diameter: 1 cm. near flower head. Vestiture: Strigose. Color: Red Purple 187A.

Flower:

*Type.*—Perfect, zygomorphic in composite head.

*Size.*—12.5 cm. wide and 2 to 5 cm deep as disc enlarges.

*Ray petals.*—In 2 or 3 series, about 80, irregular in width and length, sometimes twisted, giving the flower a ruffled look. Occasionally flatten tubes. Shape: Oblong to narrowly oblong with the tip 2 to 3 toothed. Length: Varies on one head from 3.5 to 4.7 cm long. Width: 0.7 cm on long petals and 0.9 to 1 cm on shorter petals. Texture — Satiny, soft. Vestiture — Glabrous except for bottom side where sparsely strigose.

*Disc.*—Average number of disc florets between 450 and 500. Shape — Convex becoming conic. Size — 4.8 to 5 cm wide and becoming 3.5 cm deep with maturity. Flower — 1.2 cm long, Yellow Green 146D, 5 lobed, each flower with one persistent, very stiff bract, 1.6 cm long, which gives the black to orange disc color. Pistil — 1 per floret, in ray and disc florets, 0.5 cm long, extruding, 2-branched stigma, stigma and style are Greyed Purple 187A, ovary is yellow green tinged with Greyed Purple 187A. Stamen — 5 in number, in ray and disc florets, 3 mm long, Greyed Purple 187A, anthers oval, 0.1 mm long, Orange 25C. Pollen color — No pollen, male sterile.

*Color.*—Ray, topside — Red Purple 64A. Ray, bottom side — Red Purple 59C. Disc — Greyed Purple 187A before opening and bracts Orange 25B with dark red tips, Red 46A to Greyed Purple 187A.

*Bracts* (*at the base of each head*).—Involucral bracts in six to seven leafy series, lobes lanceolate in shape, reflexed, strigose, area 3.5 to 5 cm wide.

*Bract size.*—0.3 cm wide and 0.6 to 0.8 cm long.

*Bract color.*—Yellow Green 147A.

*Bloom period.*—July through September in Canby, Oreg.

*Fragrance.*—Lovely.

*Lastingness.*—Each flower head lasts two to three weeks on the plant.

Fruit and seed: None. Plant sterile.

Diseases and pests: *Echinacea* are prone to leaf miners, powdery mildew, bacterial spots, and gray mold. Vine weevils may attack roots.

COMPARISONS TO SIMILAR *ECHINACEA*

Compared to *Echinacea purpurea* 'Ruby Giant', an unpatented plant and the parent, the new cultivar is much shorter with longer thinner leaves. The flowers of the new cultivar are a deeper red purple in color.

Compared to *Echinacea purpurea* 'Kim's Knee-Hi' (U.S. Plant Pat. No. 12,242), the new cultivar is shorter with wider flower heads that stiffly radiate rather than rigidly reflex and are colored deep red purple rather than rosy pink to purple pink. The new cultivar also has more ray flowers.

I claim:

1. A new and distinct cultivar of *Echinacea purpurea* plant named 'Little Giant', as illustrated and described.

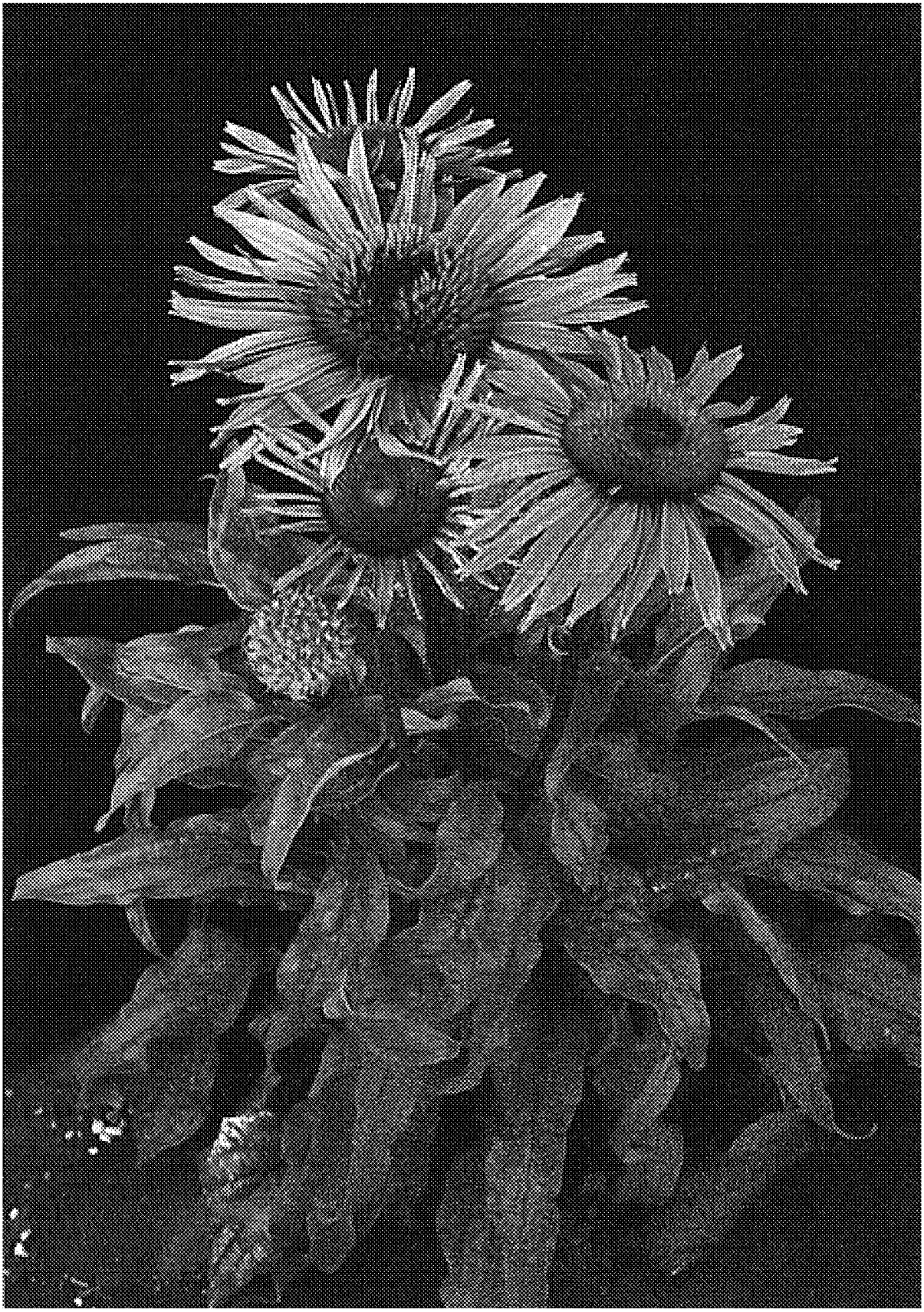

* * * * *